United States Patent [19]

Saffer

[11] Patent Number: 5,350,351
[45] Date of Patent: Sep. 27, 1994

[54] MEDICAL TREATMENT INSTALLATION HAVING AN IMAGING SYSTEM AND A THERAPY FIELD TRANSMITTER FOR TREATING A SUBJECT

[75] Inventor: Edmund Saffer, Eggolsheim, Fed. Rep. of Germany

[73] Assignee: Siemens Aktiengesellschaft, Munich, Fed. Rep. of Germany

[21] Appl. No.: 10,009

[22] Filed: Jan. 27, 1993

[30] Foreign Application Priority Data

Apr. 3, 1992 [DE] Fed. Rep. of Germany ....... 4211274

[51] Int. Cl.$^5$ .............................................. A61B 6/00
[52] U.S. Cl. .......................................... 601/2; 607/51; 607/52; 378/62; 128/653.1
[58] Field of Search ................... 128/660.03, 653.1; 378/62, 63; 607/50–52, 96, 97, 99, 102, 88, 89; 601/2, 3, 4

[56] References Cited

U.S. PATENT DOCUMENTS

| | | | |
|---|---|---|---|
| 4,796,613 | 1/1989 | Heumann et al. | 128/24 EL |
| 4,819,257 | 4/1989 | Grasser et al. | 128/24 EL |
| 4,821,729 | 4/1989 | Makofski et al. | 128/660.03 |
| 4,877,017 | 10/1989 | Hahn et al. | 128/24 EL |
| 4,979,501 | 12/1990 | Valchanov et al. | 128/24 AA |
| 4,984,575 | 1/1991 | Uchiyama et al. | 128/660.03 |
| 5,044,354 | 9/1991 | Goldhorn et al. | 128/24 EL |
| 5,070,861 | 12/1991 | Einars et al. | 128/24 EL |
| 5,081,984 | 1/1992 | Wess et al. | 128/24 EL |
| 5,090,401 | 2/1992 | Schwieker | 128/24 EL |
| 5,199,420 | 4/1993 | Artmeier | 128/24 EL |
| 5,230,329 | 7/1993 | Puppo | 128/24 EL |
| 5,284,143 | 2/1994 | Rattner | 128/653.1 |

FOREIGN PATENT DOCUMENTS 4119524 8/1992 Fed. Rep. of Germany .

Primary Examiner—K. M. Pfaffle
Attorney, Agent, or Firm—Hill, Steadman & Simpson

[57] ABSTRACT

A medical treatment installation having an imaging system and a transmitter which generates a focused therapy field, such as focused shockwaves, for treating a pathology in a region of a patient includes components for displacing the position of the focal point of the therapy field relative to the region to be treated so that the focus therapy field is successively incident at a number of locations in the region during treatment, and a mark generator, which interacts with the imaging system, for generating an indicator in the image corresponding to each of the locations of the focused therapy field in the region. The mark may identify each location at which the region has been subjected to the therapy field during treatment, so that repetitive administration of the therapy field at a location which has already been treated can be avoided.

5 Claims, 2 Drawing Sheets

MEDICAL TREATMENT INSTALLATION HAVING AN IMAGING SYSTEM AND A THERAPY FIELD TRANSMITTER FOR TREATING A SUBJECT

BACKGROUND OF THE INVENTION

The present invention is directed to a medical installation having an imaging system and a therapy field transmitter for treating a medical pathology, such as an installation for treating a bone fracture with focused acoustic waves.

A treatment installation disclosed in co-pending U.S. application Ser. No. 07/885,749, U.S. Pat. No. 5,284,143, filed May 19, 1992, entitled "Apparatus for Treating Bone Pathologies with Acoustic Energy," (Manfred Rattner), assigned to the same assignee as the present application, having an imaging system for the localization of a region to be treated, for example, a bone pathology such as fracture. The imaging system can be an ultrasound or x-ray locating system and is activated so that an image of the fracture is produced on a monitor. The fracture and a therapy field transmitter that transmits focused acoustic waves for the treatment are brought into positions relative to one another under visual control so that the acoustic waves are focused at the fracture. This ensues in a simple way when the imaging system has a fixed reference to the focus of the therapy field transmitter and when an indicator on the monitor identifies the focus of the acoustic waves. Since the imaging system comprises an image memory, the imaging field transmitter of the imaging system can be deactivated after the positioning has been carried out. The region to be treated continues to be displayed on the monitor by reading out the signals of the image memory.

It is known to place a mark (indicator) in the image of the monitor with a mouse or a light pen, this mark identifying the region to be treated, for example a location of the fracture. Dependent on this mark, the therapy field transmitter that is provided for the treatment is aligned such via a corresponding control unit that the acoustic waves are focused onto this location. The course of the fracture line of the fracture can also be traced on the picture screen of the monitor with a light pen, so that the drive of the therapy field transmitter provided for the treatment as well as the alignment thereof relative to the fracture line and the treatment thereof can automatically take place in sequence.

SUMMARY OF THE INVENTION

It is an object of the present invention to provide an improved fashioning of a medical treatment installation of the type described above.

In a medical treatment installation having an imaging system for portraying a region to be treated on a monitor, having a therapy field transmitter for transmitting a focused field for treatment which can assume different positions in the region to be treated, the above object is achieved in accordance with the principles of the present invention by providing means for generating a mark on the monitor which indicates the different positions of the focused field in the region to be treated.

An advantage of the invention is that not only the current but also prior positions of the focused field that are identified on the picture screen of the monitor.

The markings preferably identify the locations in the region to be treated at which the focused field transmitter was active; an inadvertent, multiple treatment of one location or one region is thus less likely to occur and the patient stress is reduced.

The focused field transmitter is preferably a shockwave generator, so that the medical treatment installation is particularly suitable for treating bone pathologies, for example fractures.

The imaging system is preferably as an x-ray system that includes a memory for storing an image of the region to be treated, which is supplied to the monitor. After the desired positioning of the region to be treated in the isocenter of the therapy system, an activation of the x-ray radiation is thus no longer necessary since the image of the region to be examined is stored and can be portrayed on the monitor. The x-ray radiation stress has thus been reduced.

DESCRIPTION OF THE PREFERRED EMBODIMENTS

Figure 1:
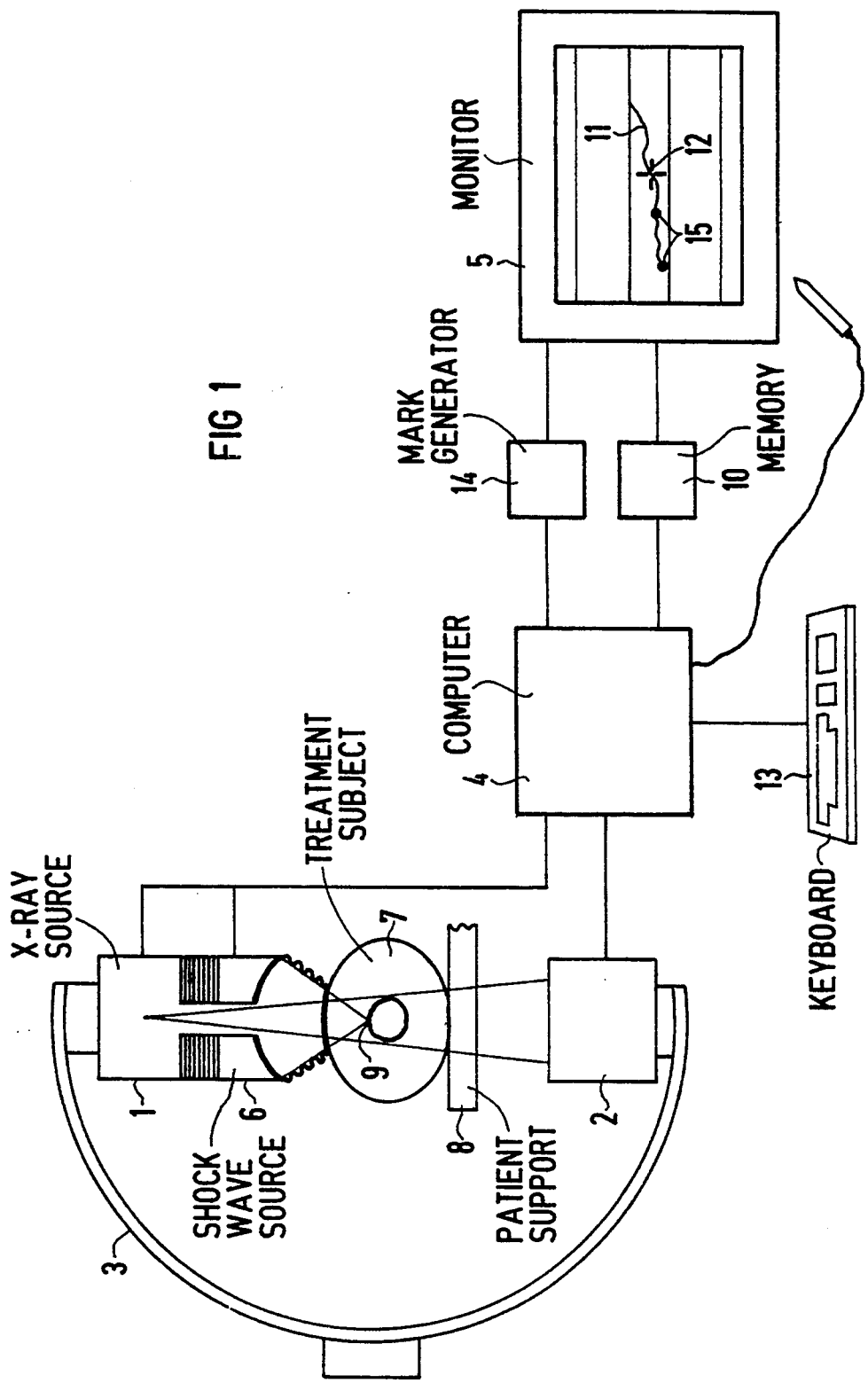
FIG. 1 is a schematic illustration of an exemplary embodiment of a medical treatment installation constructed in accordance with the principles of the present invention.

FIG. 1 shows a medical treatment installation including, for example, an x-ray radiator 1 and an x-ray image intensifier 2 that are seated opposite one another at the ends of an adjustable C-arm 3. The C-arm 3 is adjustable in the plane of the drawing as well as in a plane perpendicular thereto via its holder. The x-ray radiator 1 and the x-ray image intensifier 2 are parts of an imaging system that additionally includes a computer 4 and a monitor 5 for portraying an image of an examination region calculated by the computer 4 in a known manner from the signals of the x-ray image intensifier 2.

In the exemplary embodiment, a source for transmitting acoustic waves is provided at the x-ray radiator 1 as a therapy field transmitter. The acoustic waves propagate in the direction toward the x-ray image intensifier 2. This source is executed in the exemplary embodiment as a shockwave source 6. This shockwave source 6 can transmit focused shockwaves given a corresponding drive by the computer 4. When a treatment subject 7, for example the fracture of a thigh, is to be treated, the imaging system, or the patient support 8 supporting the thigh, is to be aligned such that the treatment region, i.e., the fracture, is located in the isocenter 9 of the C-arm 3. This ensues by activation of the imaging system under visual control on the monitor 5. For example, a suitable mark can be displayed on the picture screen of the monitor 5 for indicating the isocenter 9. Subsequently, the shockwave source 6 is adjusted into the shown, predetermined position wherein the shockwave source 6 is applied to the treatment subject 7 and the emitted shockwaves (therapy field) are focused in the isocenter 9.

The imaging system can be deactivated after the alignment of the fracture in the isocenter 9 when the computer 4 is followed by a memory 10 wherein the signals of the image produced of the examination region are stored. An image of the treatment region, wherein the fracture can also be seen as a fracture line 11, is then portrayed on the monitor 5 without stressing the treatment subject 7 with x-radiation.

A mark 12 can indicate the location at which the focused shockwaves are incident on the treatment subject 7, i.e., the fracture line 11. After the entry of the command for activating the shockwave source 6 via the keyboard 13 of the computer 4, a signal is transmitted to a mark generator 14, whose output signal is supplied to the monitor 5, so that a mark is displayed at the location of the picture screen at which the shockwaves are incident on the treatment subject 7. Such marks are identified with reference numeral 15 on the picture screen of the monitor 5 and inventively indicate the locations at which a treatment has already been carried out, i.e., at which the shockwave source 6 was active.

When a further location of the fracture line 11 is to be subsequently treated, a light pen or mouse, for example, can be connected to the computer 4 with which a mark is placed at the corresponding location of the fracture line 11. The adjustment of the shockwave source 6 for the emission of shockwaves at the location just identified can automatically ensue when adjustment means for the appropriate alignment of the shockwave source 6 are provided.

Figure 2:
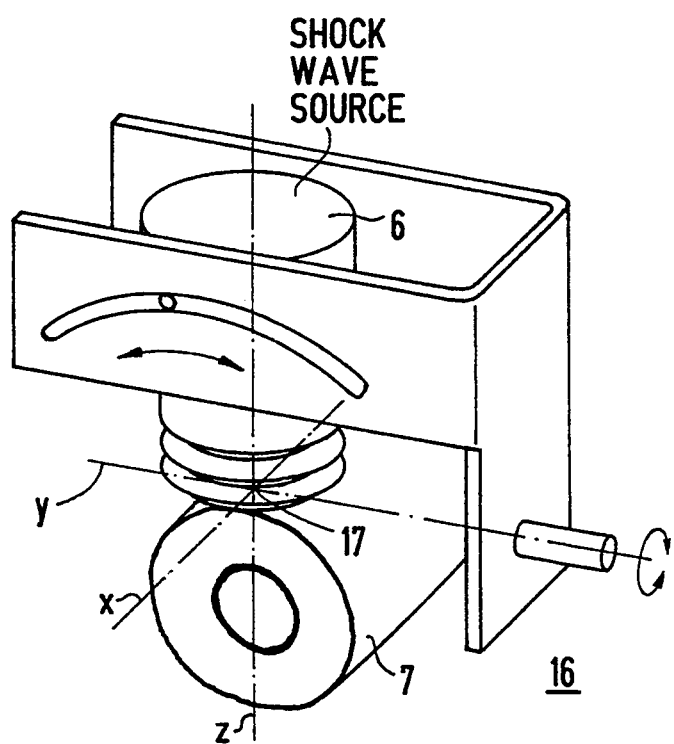
FIG. 2 shows a bearing apparatus for a combined therapy radiation and imaging radiation transmitter for use in the apparatus of FIG. 1.

As an example, FIG. 2 shows a bearing mechanism 16 for the adjustable bearing of the shockwave source 6 and (possibly) the x-ray radiator 1. In addition to the aforementioned adjustment of the shockwave source 6 and of the x-ray radiator 1 in the direction of the axis identified with Z, the mechanism 16 enables the arrangement to be pivoted around the axes identified as Y and X that lie in the same plane as the application location 17 in the applied condition of the shockwave source 6. This bearing mechanism 16 advantageously results in no relative motions arising at the transition between shockwave source 6 and subject 7 when pivoting the shockwave source 6 around the application point 17, so that a plurality of locations, for example, along the fracture line 11 (FIG. 1 ), can be treated once application has been completed without having to dislocate the subject 7 or without having to repeat the application.

The imaging system can alternatively be an ultrasound locating system within the framework of the invention. The shockwave source 6 can alternatively be seated in a separate bearing mechanism 16 (FIG. 2) specifically provided therefor independently of the x-ray radiator and can thus be adjustable. Instead of using a therapy field transmitter for transmitting acoustic waves, the medical treatment installation of the invention can alternatively employ a transmitter for transmitting electromagnetic or ionizing radiation, so that it can be utilized in heat treatment or in tumor treatment as well.

Although modifications and changes may be suggested by those skilled in the art, it is the intention of the inventor to embody within the patent warranted hereon all changes and modifications as reasonably and properly come within the scope of his contribution to the art.

I claim as my invention:

1. A medical installation for treating a region of a patient, comprising:
    imaging means for generating an image of a region to be treated of a patient;
    therapy means for generating a focused therapy field converging at a focal point for treating a pathology in said region;
    means for displacing the position of said focal point relative to said region so that said focal point of said focused therapy field is successively incident at a plurality of locations in said region during generation of said focused therapy field said therapy means being activated to generate said therapy field at each of said locations; and
    means interacting with said imaging means for generating at least a first indicator in said image corresponding to each of said locations of said focal point of said focused therapy field in said region at which said therapy means was active and a second indicator indicating the location at which the focal point is currently incident.

2. A medical treatment installation as claimed in claim 1 wherein said therapy means comprises a shockwave generator.

3. A medical treatment installation as claimed in claim 1 wherein said imaging means is an x-ray imaging system having memory means for storing the image of said region and video monitor means, connected to said memory means, for visually displaying said image.

4. A medical treatment installation as claimed in claim 1 wherein said means for displacing the position of said focal point relative to said region includes bearing means, in which said therapy means is mounted, for permitting adjustment of said therapy means around said region.

5. A medical treatment installation as claimed in claim 4 wherein said imaging means is also mounted on said bearing means.

* * * * *